US007252944B2

(12) United States Patent
Shah et al.

(10) Patent No.: US 7,252,944 B2

(45) Date of Patent: Aug. 7, 2007

(54) METHODS AND COMPOSITIONS FOR MODULATING CELL PROLIFERATION

(75) Inventors: Kavita Shah, Lafayette, IN (US); Sungjoon Kim, San Diego, CA (US)

(73) Assignee: IRM LLC, Hamilton (BM)

( * ) Notice: Subject to any disclaimer, the term of this patent is extended or adjusted under 35 U.S.C. 154(b) by 47 days.

(21) Appl. No.: 10/903,334

(22) Filed: Jul. 30, 2004

(65) Prior Publication Data

US 2005/0118663 A1 Jun. 2, 2005

Related U.S. Application Data

(60) Provisional application No. 60/491,315, filed on Jul. 30, 2003.

(51) Int. Cl.
*C12Q 1/68* (2006.01)

(52) U.S. Cl. ............................. 435/6; 435/5; 435/69.1

(58) Field of Classification Search .................... 435/6, 435/5, 69.1
See application file for complete search history.

(56) References Cited

U.S. PATENT DOCUMENTS 6,514,719 B1 * 2/2003 Bird et al. .................... 435/15

* cited by examiner

*Primary Examiner*—Ali R. Salimi
(74) *Attorney, Agent, or Firm*—Timothy L. Smith; Genomics Institute of the Novartis Research Foundation

(57) ABSTRACT

This invention provides methods for identifying novel SHMT modulators. The methods comprise first screening test agents for modulators of p38 activity and then further screening the identified modulating agents for modulators of SHMT enzyme activity. The invention further provides methods and pharmaceutical compositions for modulating cellular proliferation and for treating tumors using the novel SHMT modulators.

9 Claims, 4 Drawing Sheets

- NaCl
+ NaCl
+NaCl +1-NM-PP1
0 5 10 20 40
0 5 10 20 40
0 5 10 20 40
(min.)
Krs1
Tdh3
Hsp26
Frs2
Shm2
1 2 3 4 5 6 7 8 9 10 11 12 13 14 15

100
SHMT1 activity (%)
time (min)
0
15
30
Sorbitol
SHMT1
-
+
p38α
Shm2

METHODS AND COMPOSITIONS FOR MODULATING CELL PROLIFERATION

CROSS-REFERENCE TO RELATED APPLICATIONS

This application claims the benefit of priority under 35 U.S.C. §119(e) to U.S. Provisional Patent Application No. 60/491,315, filed Jul. 30, 2003. The disclosure of the priority application is incorporated herein by reference in its entirety and for all purposes.

FIELD OF THE INVENTION

The present invention generally relates to methods for identifying novel agents that inhibit cellular proliferation and tumorigenesis, and to therapeutic applications of such agents. More particularly, the invention pertains to novel modulators that modulate (e.g., inhibit) activities of serine hydroxymethyltransferase (SHMT), and to methods of using such modulators to modulate cellular proliferation.

BACKGROUND OF THE INVENTION

Serine hydroxymethyltransferase (SHMT) catalyzes the retro-aldol cleavage of serine to yield glycine and the hydroxymethyl group is transferred to 5,6,7,8-tetrahydrofolate to generate 5,10-methylene-$H_4$-folate. It is a ubiquitous enzyme found in all prokaryotes and eukaryotes. This enzyme plays an important role in channeling metabolites between amino acid and nucleotide metabolism (reviewed in Rao et al., Int J Biochem Cell Biol 32: 405-416, 2000). Elevated SHMT1 activity has been shown to be coupled to the higher demand of DNA synthesis in rapidly proliferating cells, particularly tumor cells (Snell et al., Br J Cancer 57, 87-90, 1988).

SHMT along with thymidylate synthase and dihydrofolate reductase constitutes the thymidylate synthase cycle. Dihydrofolate reductase and thymidylate synthase have been favourite targets for the development of anticancer drugs. A common problem encountered in clinical situations using these inhibitors is the emergence of drug resistance. The currently known inhibitors of SHMT also proved to be not entirely satisfactory. For example, the classical inhibitors of DHFR, viz. methotrexate and its structural analogs including quinazolines, failed to inhibit SHMT activity significantly.

There is a need in the art for novel SHMT-modulating agents that are useful in cancer chemotherapy. The instant invention fulfills this and other needs.

SUMMARY OF THE INVENTION

In one aspect, the present invention provides methods for identifying agents that modulate serine hydroxymethyltransferase (SHMT) activity. The methods entail (a) assaying a biological activity of p38, its homolog, or a functional equivalent in the presence of test agents to identify one or more modulating agents that modulate the biological activity of p38; and (b) testing one or more of the modulating agents for ability to modulate enzymatic activity of SHMT.

In some of the methods, the assayed biological activity of p38 is its kinase activity. Some of the methods are directed to identifying modulating agents that stimulate p38 kinase activity. In these methods, the identified SHMT modulators inhibit SHMT enzymatic activity.

In some of the methods, the assayed biological activity of p38 is its cellular level. Some of the methods are directed to identifying modulating agents that enhance p38 cellular level. In these methods, the identified SHMT modulators inhibit SHMT enzymatic activity.

In some methods, the assayed p38 kinase is human p38 MAP kinase. In some methods, the p38 homolog is yeast Hog1 kinase.

In another aspect, the invention provides methods for modulating proliferation of a cell. The methods comprise contacting the cell with a novel SHMT modulator which is identified by (a) assaying a biological activity of p38, its homolog, or a functional equivalent in the presence of test agents to identify one or more modulating agents that modulate the biological activity of p38, and (b) testing one or more of the modulating agents for ability to modulate enzymatic activity of SHMT.

In some of these methods, the assayed biological activity of p38 is its kinase activity. In some of these methods, the identified modulating agents stimulate p38 kinase activity. In these methods, the novel SHMT modulator inhibits SHMT enzymatic activity.

In some of the methods, the assayed biological activity of p38 is its cellular level. In some of these methods, the identified modulating agents enhance p38 cellular level. In these methods, the novel SHMT modulator inhibits SHMT enzymatic activity.

In some of the methods, the assayed p38 kinase is human p38 MAP kinase. In some of the methods, the p38 homolog is yeast Hog1 kinase.

In another aspect, the invention provides methods for modulating proliferation of a cell. These methods entail contacting the cell with a novel SHMT modulator which modulates enzymatic activity of SHMT. The novel SHMT modulator is identified by assaying a biological activity of p38 in the presence of test agents to identify modulating agents that modulate the biological activity of p38.

In some of these methods, the novel SHMT modulator is identified by assaying test agents for ability to stimulate p38 kinase activity. In these methods, the novel SHMT modulator inhibits SHMT enzymatic activity. Some of the methods are directed to inhibiting proliferation of the cell. In some of these methods, the cell is a tumor cell. The tumor cell can present in a subject.

A further understanding of the nature and advantages of the present invention may be realized by reference to the remaining portions of the specification and claims.

DETAILED DESCRIPTION

Figure 1:
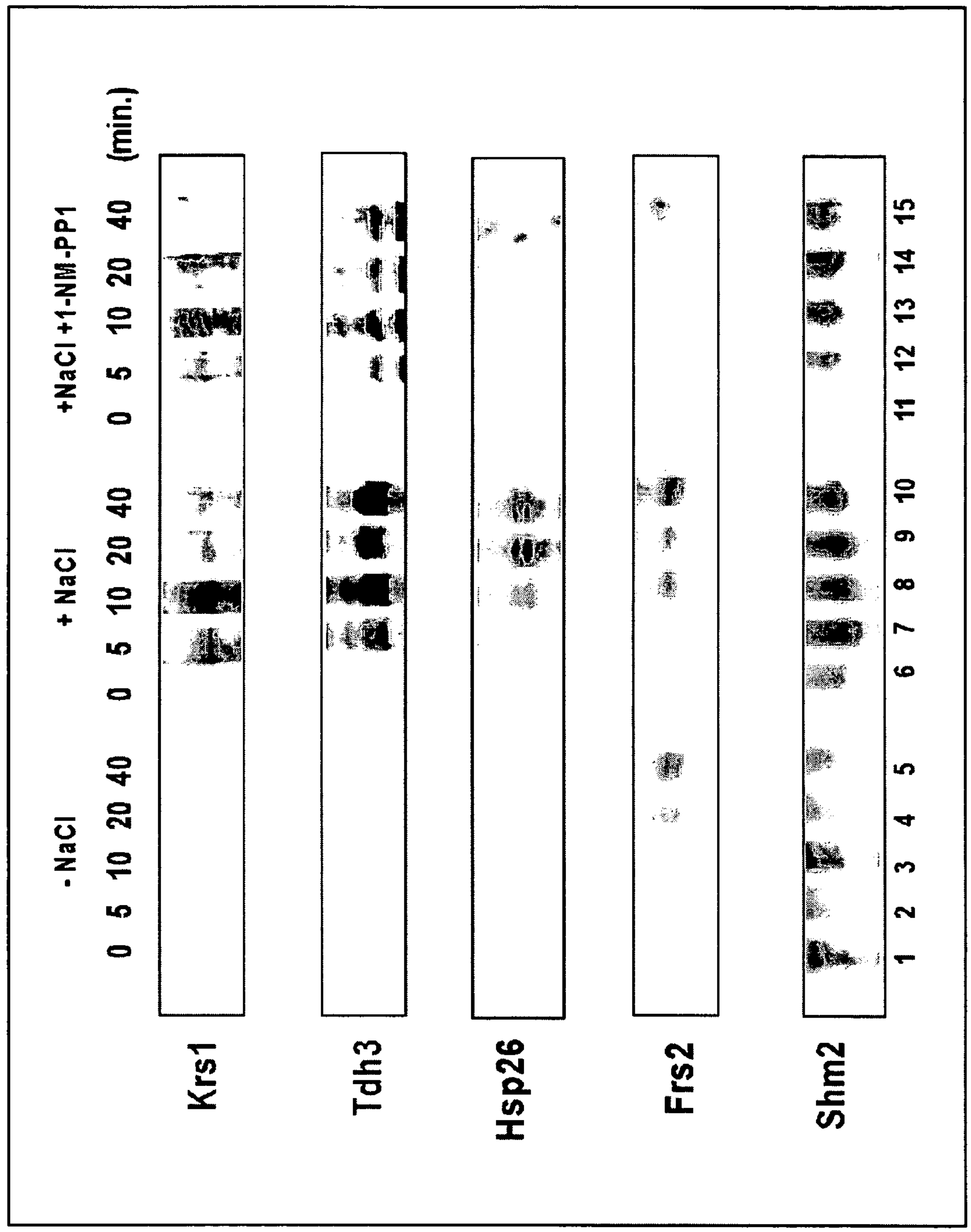
FIG. 1 shows in vivo labeling experiments that reveal several direct targets of Hog1 kinase. Autoradiogram of each candidate protein from hog1-as1 strain treated with DMSO followed by water (lanes 1 to 5), with DMSO followed by 0.9 M NaCl (lanes 6 to 10), or with inhibitor 1-NM-PP1 followed by 0.9 M NaCl (lanes 11 to 15). Cells were harvested at 0, 5, 10, 20, and 40 minutes after salt was added (as indicated at the top of the figure) and were processed as described in the experimental section.

The present invention is predicated in part on the discovery by the present inventors that human SHMT1 is an in vivo substrate of the p38 MAP kinase. In accordance with these discoveries, the present invention provides novel modulators of SHMT activities and methods for identifying such modulators. The invention also provides methods for modulating SHMT activities in cells and for treating various diseases or conditions due to abnormal cellular proliferation in a subject. The following sections provide guidance for making and using the compositions of the invention, and for carrying out the methods of the invention.

I. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

As used herein, "contacting" has its normal meaning and refers to combining two or more agents (e.g., polypeptides or small molecule compounds) or combining agents and cells. Contacting can occur in vitro, e.g., combining an agent with a target protein or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

A "heterologous sequence" or a "heterologous nucleic acid," as used herein, is one that originates from a source foreign to the particular host cell, or, if from the same source, is modified from its original form. Thus, a heterologous gene in a host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein and are generally available.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

The term "identical" or "sequence identity" in the context of two nucleic acid sequences or amino acid sequences refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well-known in the art. Optimal alignment of sequences for comparison may be conducted by the local homology algorithm of Smith and Waterman (1981) Adv. Appl. Math. 2:482; by the alignment algorithm of Needleman and Wunsch (1970) J. Mol. Biol. 48:443; by the search for similarity method of Pearson and Lipman (1988) Proc. Nat. Acad. Sci U.S.A. 85:2444; by computerized implementations of these algorithms (including, but not limited to CLUSTAL in the PC/Gene program by Intelligentics, Mountain View, Calif.; and GAP, BESTFIT, BLAST, FASTA, or TFASTA in the Wisconsin Genetics Software Package, Genetics Computer Group (GCG), 575 Science Dr., Madison, Wis., U.S.A.). The CLUSTAL program is well described by Higgins and Sharp (1988) Gene 73:237-244; Higgins and Sharp (1989) CABIOS 5:151-153; Corpet et al. (1988) Nucleic Acids Res. 16:10881-10890; Huang et al (1992) Computer Applications in the Biosciences 8:155-165; and Pearson et al. (1994) Methods in Molecular Biology 24:307-331. Alignment is also often performed by inspection and manual alignment. In one class of embodiments, the polypeptides herein are at least 70%, generally at least 75%, optionally at least 80%, 85%, 90%, 95% or 99% or more identical to a reference polypeptide, e.g., a p38 polypeptide, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 99% or more identical to a reference nucleic acid, e.g., a p38 polynucleotide, e.g., as measured by BLASTN (or CLUSTAL, or any other available alignment software) using default parameters.

The terms "substantially identical" nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "isolated" means that the material is removed from its original environment (e.g., the natural environment if it is naturally occurring). For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. A "polynucleotide sequence" is a nucleic acid (which is a polymer of nucleotides (A,C,T,U,G, etc. or naturally occurring or artificial nucleotide analogues) or a character string representing a nucleic acid, depending on context. Either the given nucleic acid or the complementary nucleic acid can be determined from any specified polynucleotide sequence.

The term "modulate" refers to a change in the cellular level or other biological activities of a reference molecule. Modulation can be up-regulation (i.e., activation or stimulation) or down-regulation (i.e. inhibition or suppression). With respect to modulation of expression level, the change can arise from, for example, an increase or decrease in expression of a reference gene, stability of mRNA that encodes the reference protein, translation efficiency, or a change in post-translational modifications or stability of the protein. The mode of action can be direct, e.g., through binding to the reference protein or to genes encoding the reference protein. The change can also be indirect, e.g., through binding to and/or modifying (e.g., enzymatically) another molecule which otherwise modulates the reference protein.

The term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "polypeptide" is used interchangeably herein with the terms "polypeptides" and "protein(s)", and refers to a polymer of amino acid residues, e.g., as typically found in proteins in nature. A "mature protein" is a protein which is full-length and which, optionally, includes glycosylation or other modifications typical for the protein in a given cell membrane.

The promoter region of a gene includes the transcription regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or an oncopromoter.

The term "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. When used with reference to a cell, the term indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

The term "subject" refers to human and non-human animals, especially mammals. It encompasses human and other mammals such as cows, horses, sheep, pigs, cats, dogs, mice, rats, rabbits, guinea pigs, monkeys.

Transcription refers to the process involving the interaction of an RNA polymerase with a gene, which directs the expression as RNA of the structural information present in the coding sequences of the gene. The process includes, but is not limited to the following steps: (1) transcription initiation, (2) transcript elongation, (3) transcript splicing, (4) transcript capping, (5) transcript termination, (6) transcript polyadenylation, (7) nuclear export of the transcript, (8) transcript editing, and (9) stabilizing the transcript.

A transcription regulatory element or sequence include, but is not limited to, a promoter sequence (e.g., the TATA box), an enhancer element, a signal sequence, or an array of transcription factor binding sites. It controls or regulates transcription of a gene operably linked to it.

A "variant" of a molecule is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

A "vector" is a composition for facilitating introduction, replication and/or expression of a selected nucleic acid in a cell. Vectors include, e.g., plasmids, cosmids, viruses, YACs, bacteria, poly-lysine, etc. A "vector nucleic acid" is a nucleic acid molecule into which heterologous nucleic acid is optionally inserted which can then be introduced into an appropriate host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes." "Expression vectors" are vectors that comprise elements that provide for or facilitate transcription of nucleic acids that are cloned into the vectors. Such elements can include, e.g., promoters and/or enhancers operably coupled to a nucleic acid of interest.

II. Methods for Screening Novel SHMT Modulators

A. General Scheme and Assay Systems

The invention employs p38 as a novel target for screening novel modulators (stimulators or inhibitors) of SHMT activities. Various biochemical and molecular biology techniques well known in the art can be employed to practice the present invention. Such techniques are described in, e.g., Sambrook et al., *Molecular Cloning: A Laboratory Manual*, Cold Spring Harbor Press, N.Y., $3^{rd}$ Ed. (2000); and Ausubel et al., *Current Protocols in Molecular Biology*, John Wiley & Sons, Inc., New York (1999).

In some methods, test agents are first assayed for their ability to modulate a biological activity of p38 ("the first assay step"). Modulating agents thus identified are then subject to further screening for ability to modulate SHMT activities, typically in the presence of p38 ("the second testing step"). Modulation of different biological activities of can be assayed in the first step. For example, a test agent can be assayed for binding to p38. The test agent can be assayed for activity to modulate expression level of p38, e.g., transcription or translation. The test agent can also be assayed for activities in modulating cellular level or stability of p38, e.g., post-translational modification or proteolysis. In some preferred embodiments, the biological activity monitored in the first assay step is the kinase activity of p38.

Once test agents that modulate p38 are identified, they are typically further tested for ability to modulate SHMT activities. If a test agent identified in the first assay step modulates cellular level (e.g., by altering transcription activity) of p38, it would indirectly modulate SHMT activities. On the other hand, if a test agent modulates an activity other than cellular level of p38, then the further testing step is needed to confirm that their modulatory effect on p38 will indeed lead to modulation of SHMT activities. For example, a test agent that modulate the kinase activity of p38 needs to be further tested in order to confirm that modulation of p38 kinase activity can result in modulation of SHMT activities.

Both stimulators and inhibitors of SHMT activities can be identified with methods of the invention. As disclosed in the Examples below, phosphorylation of SHMT by p38 results in inhibition of SHMT enzymatic activities. Therefore, modulating agents identified in the first assay step that stimulate expression or biological activities (e.g., kinase activity) of p38 are likely to inhibit SHMT enzymatic activities. Conversely, modulating agents identified in the first screening step that suppress expression or biological activities of p38 are more likely to be enhancers of SHMT enzymatic activities. Nevertheless, the exact effects on SHMT activities by the modulating agents identified in the first screening step can only be determined in the second testing step.

A variety of routinely practiced assays can be employed in the first assay step and the second testing step. Cell-based screening systems can be used to screen test agents that modulate p38 or further examine modulatory agents thus identified for ability to alter SHMT activities. For example, to identify test agents that modulate expression of p38 in the first assay step, a construct comprising a transcription regulatory element of p38 that is operably linked to a reporter gene is introduced into a host cell system. Test agents are then examined for ability to alter the reporter gene expression. The reporter gene activity (e.g., an enzymatic activity) in the presence of a test agent can be determined and compared to the activity of the reporter gene in the absence of the agent. An increase or decrease in the activity identifies a modulator of expression of p38. The reporter gene used in such systems can encode any detectable polypeptide (response or reporter polypeptide) known in the art, e.g., detectable by fluorescence or phosphorescence or by virtue of its possessing an enzymatic activity. The detectable response polypeptide can be, e.g., luciferase, alpha-glucuronidase, alpha-galactosidase, chloramphenicol acetyl transferase, green fluorescent protein, enhanced green fluorescent protein, and the human secreted alkaline phosphatase.

In addition to the first assay step, the cell-based systems can also be employed in the second testing step to examine modulating agents identified in the first step for ability to modulate SHMT activities, as detailed below. Further, other than monitoring expression of a reporter gene, the cell-based systems can also measure activities of SHMT or p38. For example, in the first assay step, the assay systems can be designed to directly monitor cellular level or a biological activity (e.g., enzymatic activity) of p38. In the second testing step, the assay system can monitor SHMT activities in the presence or absence of the modulating agents identified in the first assay step.

In the cell-based assays, the test agents or the modulating agents (e.g., peptides or polypeptides) can also be expressed from a different vector that is also present in the host cell. In some methods, a library of test agents are encoded by a library of such vectors (e.g., a cDNA library). Such libraries can be generated using methods well known in the art (see, e.g., Sambrook et al. and Ausubel et al., supra) or obtained from a variety of commercial sources.

In addition to cell based assays described above, modulators of SHMT activities can also be screened with non-cell based methods. For example, these assays can be employed to identify agents that bind to p38 or modulate expression of p38 (e.g., in the first screening step). Such methods include, e.g., mobility shift DNA-binding assays, methylation and uracil interference assays, DNase and hydroxy radical footprinting analysis, fluorescence polarization, and UV crosslinking or chemical cross-linkers. For a general overview, see, e.g., Ausubel et al., supra (chapter 12, DNA-Protein Interactions). One technique for isolating co-associating proteins, including nucleic acid and DNA/RNA binding proteins, includes use of UV crosslinking or chemical cross-linkers, including e.g., cleavable cross-linkers dithiobis (succinimidylpropionate) and 3,3'-dithiobis (sulfosuccinimidyl-propionate); see, e.g., McLaughlin (1996) Am. J. Hum. Genet. 59:561-569; Tang (1996) Biochemistry 35:8216-8225; Lingner (1996) Proc. Natl. Acad. Sci. USA 93:10712; Chodosh (1986) Mol. Cell. Biol 6:4723-4733.

Either an intact p38 gene or p38 polypeptide, or their fragments, analogs, or functional derivatives can be employed in the first assay step. Similarly, in the second testing step, the intact SHMT enzyme or polynucleotide encoding the enzyme, or their fragments, analogs, or functional derivatives can be used. The fragments that can be employed in these assays usually retain one or more of the biological activities of the target molecule (e.g., the kinase activity of p38 or the enzyme activity of SHMT). Fusion proteins containing such fragments or analogs can also be used for the screening of test agents. Functional derivatives of p38 or SHMT usually have amino acid deletions and/or insertions and/or substitutions while maintaining one or more of the bioactivities and therefore can also be used in practicing the screening methods of the present invention. A functional derivative of a polypeptide can be prepared from a naturally occurring or recombinantly expressed protein by proteolytic cleavage followed by conventional purification procedures known to those skilled in the art. Alternatively, the functional derivative can be produced by recombinant DNA technology by expressing only fragments of the polypeptide that retains one or more of their bioactivities.

B. Test Agents

Test agents that can be screened with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of SHMT activities. A number of assays are available for such screening, e.g., as described in Schultz (1998) Bioorg Med Chem Lett 8:2409-2414; Weller (1997) Mol Divers. 3:61-70; Fernandes (1998) Curr Opin Chem Biol 2:597-603; and Sittampalam (1997) Curr Opin Chem Biol 1:384-91.

Libraries of test agents to be screened with the claimed methods can also be generated based on structural studies of p38, their fragments or analogs. Such structural studies allow the identification of test agents that are more likely to bind to p38. The three-dimensional structure of p38 can be studied in a number of ways, e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Such crystal structures of p38 have been disclosed in the literature, e.g., Chang et al., Mol Cell. 9(6):1241-9, 2002; and Wilson et al., J. Biol. Chem. 271(44):27696-700, 1996. Computer modeling of p38 structure provides another means for designing test agents for screening SHMT modulators of the present invention. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system".

Modulators of the present invention also include antibodies that specifically bind to p38. Such antibodies can be monoclonal or polyclonal. Such antibodies can be generated using methods well known in the art. For example, the production of non-human monoclonal antibodies, e.g., murine or rat, can be accomplished by, for example, immunizing the animal with a p38 polypeptide or its fragment (See Harlow & Lane, Antibodies, A Laboratory Manual, Cold Spring Harbor Laboratory Press, Cold Spring Harbor N.Y.). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to a p38 polypeptide.

Human antibodies against a p38 polypeptide can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using a p38 polypeptide or its fragment.

C. Screening Test Agents for Agents that Modulate p38

A number of assay systems can be employed to screen test agents for p38 modulators. As noted above, the screening can utilize an in vitro assay system or a cell-based assay system. In this screening step, test agents can be screened for binding to p38, altering cellular level of p38, or modulating other biological activities (e.g., kinase activity) of p38.

1. Binding of Test Agents to a p38 Polypeptide

In some methods, binding of a test agent to a p38 polypeptide is determined in the first assay step. Binding of test agents to a p38 polypeptide can be assayed by a number of methods including e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The test agent can be identified by detecting a direct binding to p38, e.g., co-immunoprecipitation with p38 by an antibody directed to p38. The test agent can also be identified by detecting a signal that indicates that the agent binds to p38, e.g., fluorescence quenching.

Competition assays provide a suitable format for identifying test agents that specifically bind to a p38 polypeptide. In such formats, test agents are screened in competition with a compound already known to bind to p38. The known binding compound can be a synthetic compound. It can also be an antibody, which specifically recognizes p38, e.g., a monoclonal antibody directed against p38. If the test agent inhibits binding of the compound known to bind p38, then the test agent likely also binds p38.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using $^{125}$I label (see Morel et al., Mol. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified polypeptide bound to a solid surface or cells bearing either of these, an unlabelled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize a p38 polypeptide or its fragments onto a solid phase matrix. The solid phase matrix is then put in contact with test agents, for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing p38, the test agents are bound to the solid matrix and p38 molecule is then added.

Soluble assays include some of the combinatory libraries screening methods described herein. Under the soluble assay formats, neither the test agents nor p38 are bound to a solid support. Binding of a p38 polypeptide or fragment thereof to a test agent can be determined by, e.g., changes in fluorescence of either p38 or the test agents, or both. Fluorescence may be intrinsic or conferred by labeling either component with a fluorophor.

In some binding assays, either p38, the test agent, or a third molecule (e.g., an antibody against p38) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}$I, $^{32}$P, $^{35}$S) or a chemiluminescent or fluorescent group. Similarly, the detectable group can be a substrate, cofactor, inhibitor or affinity ligand.

2. Agents Modulating Other Activities of p38

Binding of a test agent to a p38 polypeptide provides an indication that the agent can be a modulator of p38. It also suggests that the agent may modulate SHMT activities (e.g., by binding to and modulate p38 which in turn acts on SHMT). Thus, a test agent that binds to a p38 polypeptide can be further tested for ability to modulate SHMT activities (i.e., in the second testing step outlined above). Alternatively, a test agent that binds to a p38 polypeptide can be further examined to determine its activity on p38. The existence, nature, and extend of such activity can be tested by an activity assay (e.g., assaying p38 kinase activity). Such an activity assay can confirm that the test agent binding to p38 indeed has a modulatory activity on p38.

More often, activity assays can be used independently to identify test agents that modulate activities of a p38 polypeptide (i.e., without first assaying their ability to bind to p38). These include assaying effects on expression or cellular level of p38 or assaying effects on other biological activities of p38 (e.g., its kinase activity). In general, such methods involve adding a test agent to a sample containing a p38 polypeptide in the presence or absence of other molecules or reagents which are necessary to test a biological activity of p38 (e.g., kinase activity), and determining an alteration in the biological activity of p38. In addition to assays for screening agents that modulate other biological activities of a p38 polypeptide (e.g., its kinase activity), the activity assays also encompass in vitro screening and in vivo screening for alterations in expression or cellular level of p38.

The polynucleotide and amino acid sequences of p38 are known in the art (e.g., Lee et al., Nature 372: 739-746, 1994; Han et al., Biochim Biophys Acta. 1265(2-3):224-7, 1995; and Buckley et al., J. Cell Biol. 105(6 Pt 1):2447-56, 1987). Biochemical properties of the enzyme have also been characterized. Assays of its kinase activity can be performed as described in the art, e.g., Shrode et al., J Biol Chem 272(21):13653-9, 1997; Schafer et al., J Immunol 162(2): 659-68, 1999; and Somervaille et al., Br J Haematol 120 (5):876-86, 2003. In addition to human p38α (i.e., the original p38 kinase), other p38 isoforms as well as p38 kinases from the other species (e.g., other mammalian species) may also be employed in the screening of p38 modulators. For example, mouse p38 kinase (Han et al., Science 265:808-11, 1994), p38β which has 74% amino acid identity to p38α (Jiang et al., J. Biol. Chem. 271: 17920-17926, 1996), p38γ which has 60% sequence identity to p38α (Lechner et al., Proc. Natl. Acad. Sci. USA 93: 4355-4359, 1996), and p386 (Wang et al., J Biol Chem 272: 23668-74, 1997) have all been disclosed in the art. In addition, yeast p38 homolog, Hog 1, can also substitute for p38 in the screening.

Other than screening for novel agents that directly modulate p38, the first screening step can also be directed to identify compounds which modulate activities of some known p38 modulators. For example, human kinase kinases MKK3, MKK4, and JNKK are know to phosphorylate and activate p38 (Derijard et al., Science 267: 682-5, 1995; and Lin et al., Science 268: 286-290, 1995). Therefore, agents that indirectly modulate p38 can be identified by screening test agents for ability to alter activities (e.g., kinase activity) of any of these known p38 modulators (e.g., MKK3). Such screening can be carried out using similar methods as described above. Modulators thus identified can be further tested for their effects on p38 activities. Alternatively, they can be subject to the second screening step, i.e., examination of their activities on SHMT.

D. Screening p38-Modulating Agents for SHMT Modulators

Once a modulating agent has been identified to bind to a p38 polypeptide and/or to modulate a biological activity (including cellular level) of p38, it can be further tested for ability to modulate SHMT activities. Modulation of SHMT activities by the modulating agent is typically tested in the presence of p38. For example, when a cell-based screening system is employed, the cells may endogenously express p38 while labeled SHMT can be expressed from an expression vector that has been transfected into the host cell. Alternatively, p38 can be expressed from an expression vector that has been introduced into a host cell.

SHMT exists both in the cytosol and the mitochrondria. Genes encoding both enzymes have been mapped, cloned, and characterized (Garrow et al., J. Biol. Chem. 268: 11910-11918, 1993; Stover et al., J. Biol. Chem. 272: 1842-1848, 1997; and Girgis et al., Gene 210: 315-324, 1998). Expression of the genes are cell specific, suggesting a function for the gene in regulating metabolic fluxes in different types of cells. Although the cytosolic gene was longer than its mitochondrial counterpart, there is considerable sequence similarity between the two isozymes. Either of these two enzymes or polynucleotides encoding the enzymes can be employed in the screening methods of the present invention. In addition, SHMT from other species or their homologs may also be used. There are at least 35 SHMT sequences reported in the SWISS-PROT and GENE-BANK datababses. For example, SHMT homologs from rabbit (Byrne et al., Biochem. J. 286: 117-123, 1992), pea (Turner et al., J. Biol. Chem. 267: 13528-13534, 1992), yeast (McNeil et al., J. Biol. Chem. 269: 9155-9165, 1994), and sheep (Jagath-Reddy et al., Eur. J. Biochem. 230: 533-537, 1995) may be employed in the second screening step.

As noted above, various assay formats can be employed in this screening step. Similar to the first screening step for identifying agents that modulate p38, modulation of SHMT activities can be determined in non-cell based assay systems or cell-based assays. In some methods, effects of the identified p38 modulators on SHMT are examined in an in vitro enzymatic assay, e.g., as described in the Examples below. In other methods, activities of p38 modulators on SHMT are assayed in an in vivo cell based system. An example of such in vivo system is described in the Examples below. Briefly, labeled SHMT can be expressed from an expression vector that has been introduced into cultured cell lines. p38 pathway is then stimulated (e.g., by sorbitol) in the presence or absence of a p38 modulating agent identified in the first screening step. Thereafter, SHMT can be isolated from the cells at certain time points after stimulation. Enzymatic activities of SHMT can then be measured with the assays described herein. If the presence of the p38 modulating agent results in a difference in SHMT enzymatic activity, an SHMT modulator of the present invention is identified.

Any readily transfectable mammalian cell line may be employed to practice methods of the invention. For example, other than the HEK 293 cells described in the Examples, HepG2 cell; Hep3B cell (Blanchard et al., Mol. Cell. Biol. 12: 5373-85, 1992); COS (e.g., ATCC No. CRL 1650 or 1651); BHK (e.g., ATCC No. CRL 6281); CHO-KI (ATCC No. CCL 61), HeLa (e.g., ATCC No. CCL 2), and NS-1 cells may also be used in the screening. General methods of cell culture, transfection, and reporter gene assay have been described in the art, e.g., Ausubel, supra; and Transfection Guide, Promega Corporation, Madison, Wis. (1998).

IV. Therapeutic Applications

Elevated SHMT activity appears to be required for the increased demand for DNA synthesis in rapidly proliferating cells, particularly tumor cells. As indicated in the Examples below, the present inventors discovered that SHMT is a physiological substrate of human p38 MAP kinase. Phosphorylation of SHMT1 by p38 reduces its enzymatic activity. Thus, modulating p38 activity could lead to alteration (e.g., inhibition) of SHMT enzymatic activity. As a result, p38 activators of the present invention could provide means for inhibition of tumor-genesis or treatment of cancer.

Accordingly, the invention provides therapeutic compositions and methods for preventing or treating diseases and conditions related to abnormal cellular proliferation, such as various cancers. Modulation of SHMT activity is also useful for preventing or modulating the development of such diseases or disorders in an animal suspected of being, or known to be, prone to such diseases or disorders. To inhibit cellular proliferation or to treat cancer, a subject can be administered with any a number of the novel modulators identified in accordance with the present invention. In some methods, an SHMT modulator is introduced directly to a subject (e.g., a human or a non-human mammal). In preferred embodiments, a small molecule p38 modulator that enhances p38 activities and hence inhibits SHMT enzymatic activities can be administered to a human subject to treat tumors.

A. Disease and Disorders Amenable to Treatment

Many clinical conditions or disease states are linked to abnormal cell proliferation. Such disease states and disorders include those involving the hyperproliferation of cells such as, e.g., a tumor (neoplasm) or malignant tumor. All these diseases and conditions are amenable to treatment with methods and compositions of the present invention. Examples of tumors that can be treated with methods and compositions of the present invention include but are not limited to skin, breast, brain, cervical carcinomas, testicular carcinomas. They encompass both solid tumors or metastatic tumors.

Cancers that can be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., colon carcinoma, and cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

Disease states other than cancer which may be treated by the methods and compositions also include restenosis, autoimmune disease, arthritis, graft rejection, inflammatory bowel disease, proliferation induced after medical procedures such as surgery, angioplasty, and the like. In some methods, cells not in a hyper or hypo proliferation state (abnormal state) are the subject of treatment. For example, during wound healing, the cells may be proliferating "normally", but proliferation enhancement may be desired. Similarly, in the agriculture arena, cells may be in a "normal"

state, but proliferation modulation may be desired to enhance a crop by directly enhancing growth of a crop, or by inhibiting the growth of a plant or organism which adversely affects the crop. Thus, therapeutic applications of the present invention include treatment of individuals or agricultural crops with any one of these disorders or states.

B. Pharmaceutical Compositions

The SHMT modulators of the present invention can be directly administered under sterile conditions to the subject to be treated. The modulators can be administered alone or as the active ingredient of a pharmaceutical composition. Therapeutic composition of the present invention can also be combined with or used in association with other therapeutic agents.

Pharmaceutical compositions of the present invention typically comprise at least one active ingredient together with one or more acceptable carriers thereof. Pharmaceutically carriers enhance or stabilize the composition, or to facilitate preparation of the composition. Pharmaceutically acceptable carriers are determined in part by the particular composition being administered (e.g., nucleic acid, protein, modulatory compounds or transduced cell), as well as by the particular method used to administer the composition. They should also be both pharmaceutically and physiologically acceptable in the sense of being compatible with the other ingredients and not injurious to the subject. This carrier may take a wide variety of forms depending on the form of preparation desired for administration, e.g., oral, sublingual, rectal, nasal, or parenteral. For example, the SHMT modulator can be complexed with carrier proteins such as ovalbumin or serum albumin prior to their administration in order to enhance stability or pharmacological properties.

There are a wide variety of suitable formulations of pharmaceutical compositions of the present invention (see, e.g., *Remington: The Science and Practice of Pharmacy*, Mack Publishing Co., 20$^{th}$ ed., 2000). Without limitation, they include syrup, water, isotonic saline solution, 5% dextrose in water or buffered sodium or ammonium acetate solution, oils, glycerin, alcohols, flavoring agents, preservatives, coloring agents starches, sugars, diluents, granulating agents, lubricants, and binders, among others. The carrier may also include a sustained release material such as glyceryl monostearate or glyceryl distearate, alone or with a wax.

The pharmaceutical compositions can be prepared in various forms, such as granules, tablets, pills, suppositories, capsules, suspensions, salves, lotions and the like. The concentration of therapeutically active compound in the formulation may vary from about 0.1-100% by weight. Therapeutic formulations are peprared by any methods well known in the art of pharmacy. See, e.g., Gilman et al., eds., Goodman and Gilman's: The Pharmacological Bases of Therapeutics, 8th ed., Pergamon Press, 1990; Remington: The Science and Practice of Pharmacy, Mack Publishing Co., 20$^{th}$ ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

C. Dosages and Modes of Administration

The therapeutic formulations can be delivered by any effective means which could be used for treatment. Depending on the specific SHMT modulators to be administered, the suitable means include oral, rectal, vaginal, nasal, pulmonary administration, or parenteral (including subcutaneous, intramuscular, intravenous and intradermal) infusion into the bloodstream.

For parenteral administration, SHMT modulators (including polynucleotides encoding SHMT modulators) of the present invention may be formulated in a variety of ways. Aqueous solutions of the modulators may be encapsulated in polymeric beads, liposomes, nanoparticles or other injectable depot formulations known to those of skill in the art. The nucleic acids may also be encapsulated in a viral coat.

Additionally, the SHMT modulators of the present invention may also be administered encapsulated in liposomes. The compositions, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The compositions may be supplemented by active pharmaceutical ingredients, where desired. Optional antibacterial, antiseptic, and antioxidant agents may also be present in the compositions where they will perform their ordinary functions.

The therapeutic formulations can conveniently be presented in unit dosage form and administered in a suitable therapeutic dose. A suitable therapeutic dose can be determined by any of the well known methods such as clinical studies on mammalian species to determine maximum tolerable dose and on normal human subjects to determine safe dosage. Except under certain circumstances when higher dosages may be required, the preferred dosage of an SHMT modulator usually lies within the range of from about 0.001 to about 1000 mg, more usually from about 0.01 to about 500 mg per day.

The preferred dosage and mode of administration of an SHMT modulator can vary for different subjects, depending upon factors that can be individually reviewed by the treating physician, such as the condition or conditions to be treated, the choice of composition to be administered, including the particular SHMT modulator, the age, weight, and response of the individual subject, the severity of the subject's symptoms, and the chosen route of administration. As a general rule, the quantity of an SHMT modulator administered is the smallest dosage that effectively and reliably prevents or minimizes the conditions of the subjects. Therefore, the above dosage ranges are intended to provide general guidance and support for the teachings herein, but are not intended to limit the scope of the invention.

In some applications, a first SHMT modulator is used in combination with a second SHMT modulator in order to modulate SHMT activities to a more extensive degree than cannot be achieved when one SHMT modulator is used individually.

EXAMPLES

The following examples are provided to illustrate, but not to limit the present invention.

Example 1

Methods and Assays

Osmosensitive phenotype assay: Yeast media were prepared as described (Sherman, Methods Enzymol 194, 3-21, 1991). Yeast transformations were performed using lithium acetate procedure (Schiestl and Gietz, Curr Genet 16, 339-46, 1989). The plasmid shuffle method was performed as previously described (Boeke et al., Methods Enzymol 154, 164-75, 1987) using 5-fluoroorotic acid (5-FOA). For genomic integration, the hog1 gene containing the T100G substitution was transformed into the RSY580 strain (MATα ura3-52, trp1Δ63, leu2Δ1) and FOA-resistant candidate strains were isolated. The hog1 mutant alleles were verified by the gap repair method (Orr-Weaver et al., Methods Enzymol 101, 228-45, 1983). To test the osmosensitive phenotype of the hog1 mutant strains, cultures of both wild type (wt) and hog1-as1 mutant strains were serially diluted and spotted onto YPD plates containing 0.9 M NaCl or 0.9 M NaCl plus 1-NM-PP1 in varying concentrations (0.5 to 5 μM).

Genome-wide expression analysis: Total RNA preparation from hog1-27 strain was performed as described previously (Holstege et al., Cell 95, 717-28, 1998). To monitor the changes in expression caused by specific inhibition of Hog1 kinase, cultures of either wt or hog1-27 were incubated with 1-NM-PP1 (2 μM) for 30 minutes before harvesting (for control, 0.002% DMSO was added). To monitor the effect of osmotic stress, sodium chloride was added into either inhibitor-treated or DMSO-treated cultures to a final concentration of 0.9 M.

The preparation of probe and the procedure for microassay experiments was performed as described in the literature. The output files from the scanner were uploaded into the GNF chip informatics server and expression profiles were analyzed using a built-in analysis program, ANOVA. Search for the common transcriptional regulatory elements was done using the promoter database of *Saccharomyces cerevisiae* at the Cold Spring Harbor Laboratory.

Preparation of [$\gamma$-$^{32}$P] N$^6$(Phenethyl)ATP: [$\gamma$-$^{32}$P] N$^6$ (Phenethyl) ATP was synthesized as described in Shah and Shokat, Chem Biol 9, 35-47, 2002.

Preparation of Hog1 kinase and in vitro kinase assay: The Hog1 proteins were expressed as GST-fusion proteins using pXZ134 (Vernet et al., Gene 52, 225-33, 1987) from hog1 deletion strain. For activation of Hog1 kinase, constitutively active Pbs2 kinase (Pbs2-EE) (Alessi et al., Embo J 13, 1610-9, 1994) was generated in *E. coli* (Bilsland-Marchesan et al., 2000). Constitutively active Hog1 kinase was created by substituting phenylalanine 318 by serine (Bell et al., J Biol Chem 276, 25351-8, 2001) and purified as described previously (Posas et al., Cell 86, 865-75, 1996, 1996). The enzymatic activity of the Hog1 kinase was measured with myelin basic protein as described previously (Liu et al., Chem Biol 6, 671-8, 1999). Active p38α MAP kinase was purchased from Upstate Inc. (Waltham, Mass.).

Whole cell lysate (WCL) from *Saccharomyces cerevisiae* was prepared as described (Ausubel, supra). WCL was fractionated with P-11 column (Whatman) by step-elution with increasing concentration of potassium acetate (100 mM, 200 mM, 400 mM, 600 mM, and 1 M). For in vitro labeling of yeast proteins from WCL or from fractionated lysate was performed as described (Shah and Shokat, Chem Biol 9, 35-47, 2002).

In vivo substrate labeling: Phosphate-depleted selective media was prepared as described previously (Posas et al., Cell 86, 865-75, 1996) with minor modifications. The hog1-as1 mutant strain containing each candidate gene was generated by transforming the expression construct of each candidate gene (pYEX-4T inducible expression vector system (BD science), gift from Dr. Elizabeth Winzeler). Same volume of cultures were harvested at 0, 5, 10, 20, and 40 min, cell lysate was prepared and GST-fused protein was captured by glutathione sepharose beads (Pharmacia). Labeled proteins were detected using 8-12% gradient SDS PAGE gels, electroblotting on PVDF membrane and autoradiography.

2D gel electrophoresis and MS spectrometry: 20-40 μg of WCL or fractionated lysates were labeled in a kinase reaction. 2D gel electrophoreses of labeled samples were carried out by Kendrick Labs (Madison, Wis.) with 2% pH 4-10 ampholines at 9600 volt-hrs. The gels were strained with Coomassie Brilliant Blue R-250, dried and exposed to Kodak X-OMAT AR film. Gel spots were manually excised and automatically processed for peptide mapping experiments using a Micromass MassPREP Station in conjunction with manufacturer specified protocols. MALDI mass spectra were obtained automatically using a Micromass M@LDI-R TOF MS, with ACTH fragment 18-39 as a Lockmass reference. Protein identification searches were performed using MASCOT (Matrix Sciences).

Enzymatic assay for serine hydroxymethyltransferase 2 (Shm2): GST-Shm2 was purified from a yeast strain as described above and its enzymatic activity was measured as described earlier (Krishna Rao et al., Biochem J 343 Pt 1, 257-63, 1999) with minor modifications. To measure the effect of either Hog1-as1 or p38 kinases, Shm2 enzyme was pre-incubated with each kinase in presence of either 1 mM PE-ATP (for Hog1-as1) or 1 mM ATP (for p38) for 30 min at RT before adding to the reaction mixture.

*Transfection and retroviral infection*: SHMT1 (human homolog of yeast Shm2) with a C-terminal myc tag was cloned into pBabe puro plasmid and was transiently transfected into Bosc 23 cells using Effectene (Qiagen) as manufacturer's protocol. The harvested retroviruses was added to 5×10$^5$ HEK-293 cells for infection. After 48 hours the infected cells were selected in the presence of 2.5 □g/mL of puromycin. SHMT1-HEK293 cells were cultured in DMEM with 10% Bovine Calf Serum (BCS) and were serum-starved for 24 hr in DMEM with 0.5% BCS.

*Transient transfection and SHMT1 assay: MKK6*b was cloned into pcDNA6Hismyc B vector (Invitrogen) and MKK6b-EE was further generated using Quick change protocol (Stratagene). Transient transfection of MKK6b-EE into SHMT1-HEK 293 cells was carried using Lipofectamine 2000 (Invitrogen) according to the manufacturer's protocol. Immunoprecipitation procedure for SHMT1 from transfected cells was described previously (Shah and Shokat, Chem Biol 9, 35-47, 2002). SHMT1 enzymatic assay was carried out exactly as Shm2 assay as described above. SHMT1 or phosphorylated form of p38α was detected by immunobloting with either c-myc antibody (Santa Cruz) or phospho-p38 antibody (Cell Signal) using West pico supersignal kit (Pierce).

Example 2

Identification of novel Hog1 substrates and mammalian homologs

To delineate the role of Hog1 kinase in osmotic stress induced transcriptional response, we investigated the genome-wide expression pattern of the hog1-as1 mutant strain treated with salt and 1-NM-PP1.

For DNA micro-array experiments, total RNAs were isolated from both the wt strain and the hog1-as1 mutant strain (hog1-27) treated with DMSO (WT+DMSO, MUT+DMSO), salt and DMSO (WTS+DMSO, MUTS+DMSO), salt and inhibitor (WTS+1-NM-PP1, MUTS+1-NM-PP1).

For each experiment, RNA samples were prepared in duplicates, followed by the preparation of the corresponding biotinylated cRNA probes and hybridized to Yeast Genome S98 arrays (Affymetrix). Two expression profiles were first examined between duplicate samples to ensure reproducibility and the whole procedure was repeated three times. The set of genes exhibiting similar fold changes in these results was consistent and therefore was used for further comparison. To analyze the number of genes affected by salt addition, expression profiles of MUTS+DMSO versus MUT+DMSO were compared by ANOVA (Brazma and Vilo, 2000). The expressions of 874 genes in the mutant strain were changed more than 2.5 fold by the addition of salt. Thus, the analysis covered almost the full complement of genes known to be affected by osmotic stress.

The effect of inhibition in the hog1-as1 mutant strain was examined by comparing the expression profiles of MUTS+1-NM-PP1 versus MUTS+DMSO. Interestingly, this comparison showed only 96 genes to be affected more than 2-fold, out of which 15 were upregulated and 81 were downregulated by the addition of 1-NM-PP1. Significantly, in the wt strain only 11 genes were affected by addition of the inhibitor, confirming that the effect of the inhibitor on the hog1-as1 strain is specific. Secondly, almost all of the 96 genes whose expression was specifically altered by the inhibition of Hog1 kinase, have also been reported to change upon osmotic stress in several databases. This result suggests that these 96 genes are not a random assortment of genes but rather a highly selective subset of genes directly controlled by Hog1 upon osmotic shock.

Further analysis indicates that only 75 genes out of the total of 874 osmo-responsive genes are in effect downstream of Hog1. In addition, the data identified five novel in vivo substrates of Hog1 in yeast cell extracts using Hog1-as1 and $N^6$(Phenethyl)ATP (PE-ATP). It was found that Krs1, Tdh3, Frs2, Hsp26 and Shm2 are phosphorylated in a Hog1 dependent manner in vivo upon osmotic shock (FIG. 1).

Example 3

Hog1-mediated phosphorylation modulates the enzymatic activity of Shm2 in vitro This Example demonstrates that Shm2 is a physiological substrate of Hog1 both upon osmotic stress and constitutive activation.

One of the identified novel substrates of Hog1, Shm2, is noteworthy since several groups have reported elevated SHMT1 (the mammalian counterpart of yeast Shm2) activity in various cancer cells and tumor tissues, e.g., human colon carcinomas (Snell et al., Br J Cancer 57, 87-90, 1988). Since our results show that Shm2 could be phosphorylated by Hog1 directly in response to external stimuli, we investigated whether this phosphorylation event plays any role in controlling its activity.

Figure 2:
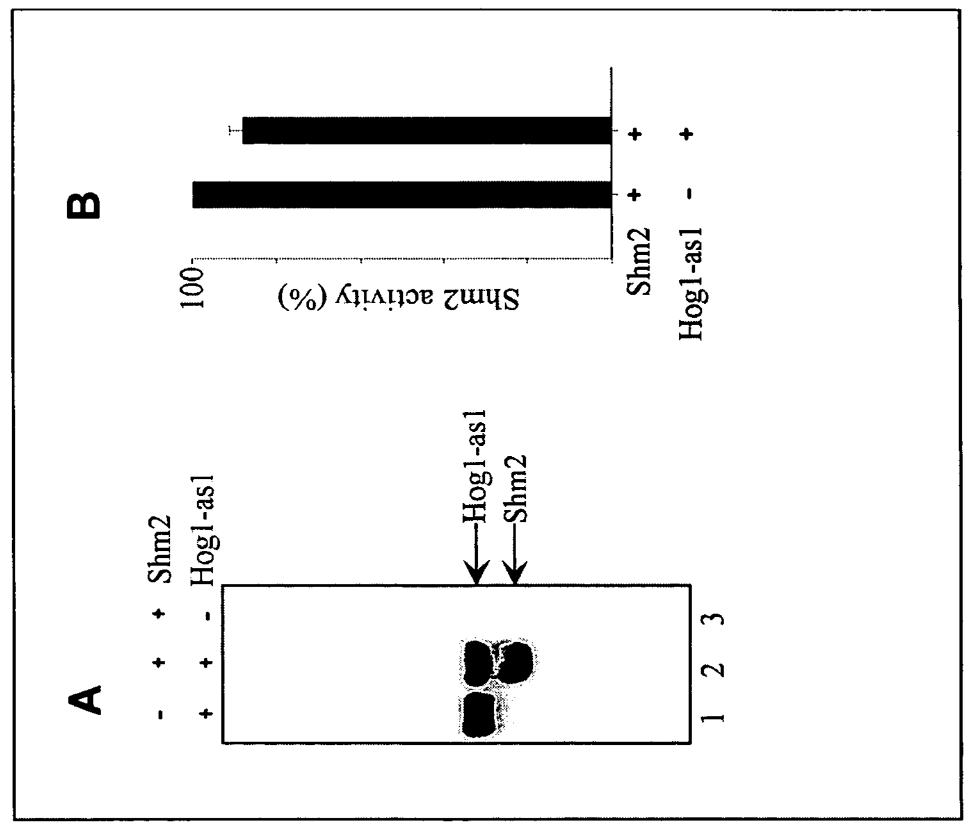
FIGS. 2A-2D show the effect of phosphorylation by Hog1-as1 or p38$\alpha$ on the Shm2 activity. A) Autoradiograms of labeled Shm2 after incubation with Hog1-as1 (lane 2) or buffer (lane 3) in the kinase reaction using [$\gamma$-$^{32}$P] PE-ATP. For control, Hog1-as1 (lane 1) was added into the reaction mixture without Shm2. The arrows indicate the positions of GST-Hog1, GST-Shm2 proteins on the gel. B) Shm2 enzymatic activities after pre-incubation with PE-ATP alone (first column) and Hog1-as1 and PE-ATP (second column). C) Autoradiograms of labeled Shm2 after incubation with p38α (lane 2) or buffer (lane 3) in the kinase reaction using [$\gamma$-$^{32}$P] ATP. For control, p38α (lane 1) was added into the reaction mixture without Shm2. The arrows indicate the positions of GST-Shm2 and p38α (from top to bottom) proteins on the gel. D) Shm2 enzymatic activities after pre-incubation with ATP alone (first column) and p38α and ATP (second column).
Figure 2:
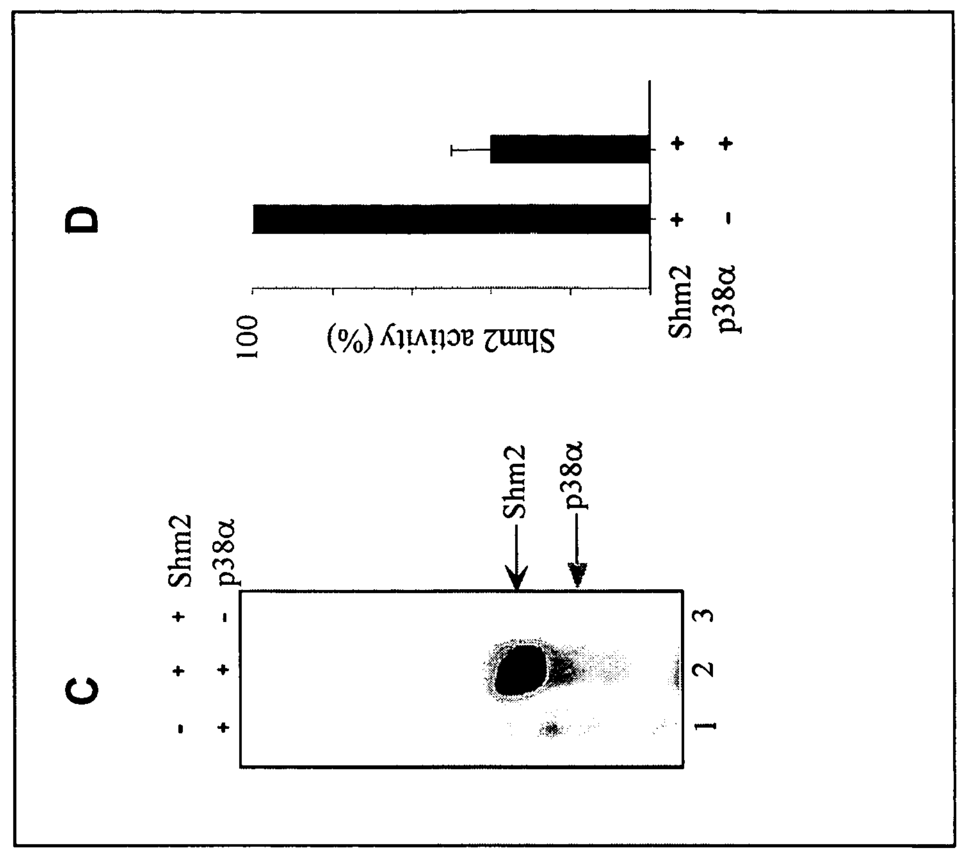

GST-Shm2 expressed in *S. cerevisiae* was found to be efficiently phosphorylated in an in vitro kinase assay by Hog1 (FIG. 2A, compare lanes 2 and 3 for Hog1). To determine Shm2 activity, we measured the transfer of $C^{14}$-labeled one-carbon unit as described in the Krishna Rao et al., Biochem J 343 Pt 1, 257-63, 1999. In order to estimate the effect of phosphorylation, Shm2 was pre-incubated with or without Hog 1 kinase, prior to the $C^{14}$ transfer reaction. As shown in FIG. 2B, Shm2 activity decreases only when both kinase and ATP were present during the pre-incubation step. This result clearly demonstrates that Hog1 dependent phosphorylation down-regulates Shm2 enzymatic activity in vitro. Furthermore, it suggests that there are alternate pathways at the post-translational level to divert biosynthetic activities of yeast cells from cell proliferation to cell survival upon osmotic stress, in addition to controlling at the transcriptional level (Gasch et al., Mol Biol Cell 11, 4241-57, 2000; and Rep et al., Mol Cell Biol 19, 5474-85, 2000).

Example 4 p38-mediated phosphorylation modulates the enzymatic activity of SHMT1 in vitro and in vivo This Example demonstrates that the mammalian homolog of Shm2, SHMT1, is a novel physiological substrate of p38 MAP kinase, and that phosphorylation of SHMT1 by p38 reduces its enzymatic activity, revealing a potential cancer-modulating property of p38 MAP kinase.

As our results suggested an important role of Hog1 in modulating the enzymatic activity of Shm2 by phosphorylation, we wondered if p38α MAP kinase (human homolog of Hog1) has the same ability to control Shm2 or SHMT1 activity. In vitro kinase assays using p38α revealed both Shm2 (FIG. 2C, compare lanes 2 and 3) and SHMT1 (data not shown) as direct substrates of p38 MAP kinase. More importantly, our results showed a strong modulation of both Shm2 and SHMT1 enzymatic activities upon phosphorylation by p38 MAP kinase in vitro (~50% for Shm2 in FIGS. 2D and 30% for SHMT1 in FIG. 4, respectively).

Figure 3:
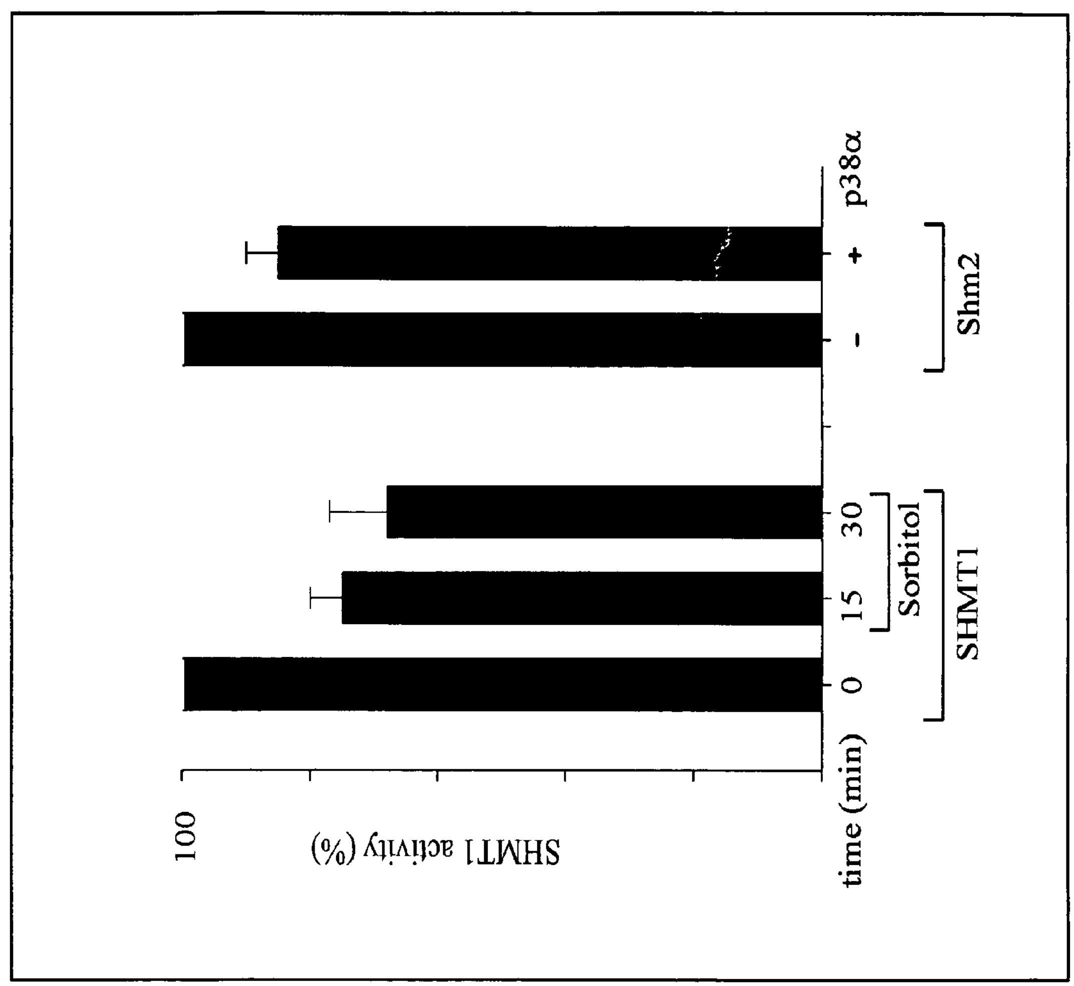
FIG. 3 shows reduced SHMT1 activity upon sorbitol-induced osmotic stress. Serum-starved SHMT1-HEK293 cells were left untreated (lane 1) or treated for 15 min. (lane 2) or 30 min. (lane 3) with 0.3 M sorbitol. For reaction control, samples containing purified GST-Shm2 pre-incubated with (lane 4) or without (lane 5) p38α MAP kinase, were included in the assay.
Figure 4:
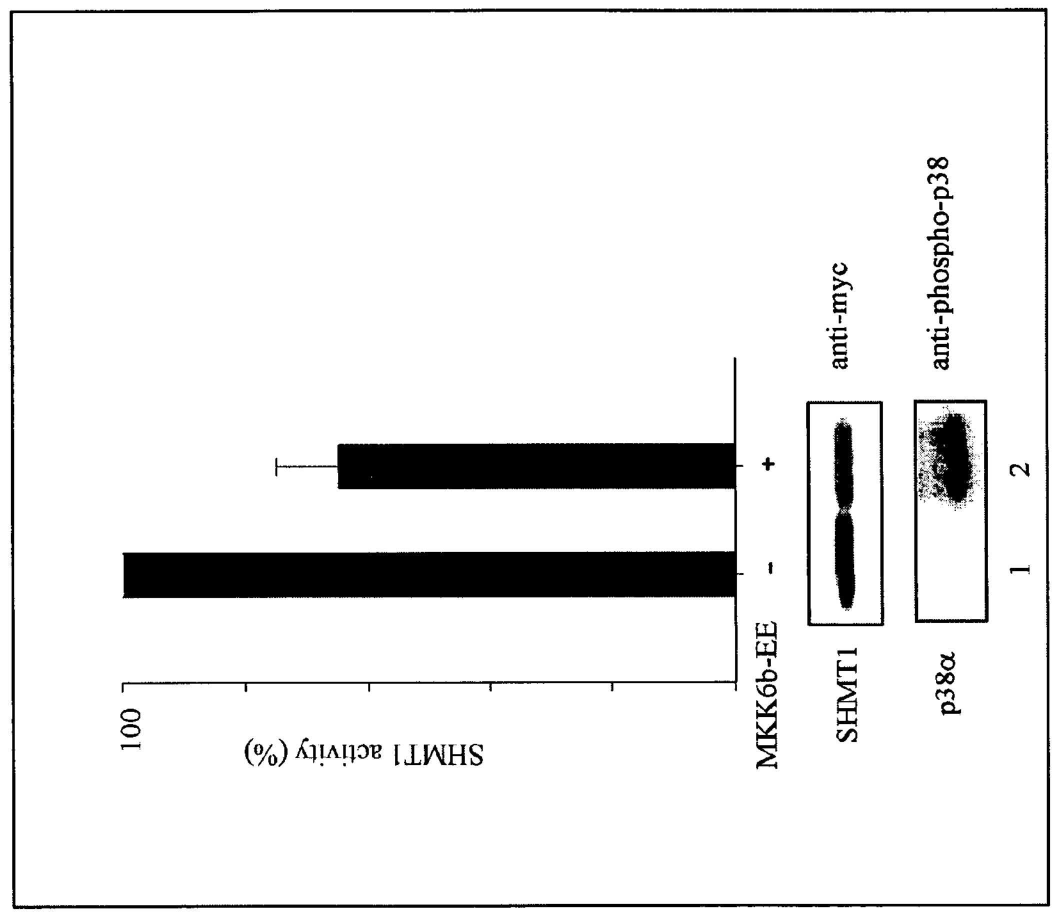
FIG. 4 shows that in vivo phosphorylation of p38 using MKK6 reduces SHMT1 enzymatic activity. SHMT1 activity was measured from SHMT1-HEK293 cells transfected with no DNA (lane 1) or with MKK6b-EE (lane 2). The amount of SHMT1 was visualized by immunoblot with 1/10th of the immunoprecipitated material using anti-myc antibody ('SHMT1'). Phosphorylation of p38α from equal protein amounts of whole cell lysate was visualized by immunoblot using an antibody against the phosphorylated form of p38α ('p38').

Finally, to investigate whether SHMT1 was also an in vivo target of p38 MAP kinase, myc-tagged SHMT1 expressing HEK 293 stable cells were generated. The p38 MAP kinase pathway was stimulated using sorbitol in 293 and SHMT1-293 cells, which showed phosphorylation of p38 in a time dependent manner as reported earlier (Alpert et al., J Biol Chem 274, 22176-83, 1999). SHMT1 was immunoprecipitated at different time points after stimulation and its enzymatic activity was measured as described above. Our results displayed decreased activity of SHMT1 as a result of sorbitol treatment (FIG. 3, compare lane 2 or 3 with lane 1). Since the sorbitol-induced pathway is also known to enhance JNK activation, in addition to that of p38 (Kayali et al., Diabetes 49, 1783-93, 2000), we generated the constitutively active form of MKK6b (MKK6b-EE), which only activates p38 (Alpert et al., J Biol Chem 274, 22176-83, 1999). Transient transfection of MKK6b-EE resulted in the activation of p38 and a strong modulation of SHMT1 activity (FIG. 4).

These results clearly suggest that p38α has the ability to control SHMT1 activity, in vitro and in vivo, resulting in significant downregulation of its enzymatic activity. Further, we demonstrated the role of SHMT1 in controlling cellular proliferation. Specifically, introduction of MKK6EE increases doubling time of myc-null cells (HO15.19). In addition, p38 phosphorylation increases doubling time of dominant-negative myc-containing COS-7 cell. Since there is a positive correlation between SHMT activity and the growth rate of tumor cells, our results suggest that p38α has a unique cancer-modulating property by controlling SHMT1 enzymatic activity important for cancerous growth.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, patents and patent applications cited herein are hereby expressly incorporated by reference in their entirety and for all purposes as if each is individually so denoted.

We claim:

1. A method for identifying an agent that modulates serine hydroxymethyltransferase (SHMT) activity, the method comprising:

(a) assaying a biological activity of p38 or its homolog in the presence of test agents to identify one or more modulating agents that modulate the biological activity of p38; and (b) testing one or more of the modulating agents for ability to modulate enzymatic activity of SHMT; thereby identifying an SHMT modulator that modulates SHMT activity.

2. The method of claim 1, wherein the biological activity of p38 is its kinase activity.

3. The method of claim 2, wherein the modulating agents stimulate p38 kinase activity.

4. The method of claim 3, wherein the SHMT modulator inhibits SHMT enzymatic activity.

5. The method of claim 1, wherein the biological activity of p38 is its cellular level.

6. The method of claim 5, wherein the modulating agents enhance p38 cellular level.

7. The method of claim 6, wherein the SHMT modulator inhibits SHMT enzymatic activity.

8. The method of claim 1, wherein the p38 is human p38 MAP kinase.

9. The method of claim 1, wherein the p38 homolog is yeast Hog1 kinase.

* * * * *